US010322988B2

(12) United States Patent
Reed et al.

(10) Patent No.: US 10,322,988 B2
(45) Date of Patent: Jun. 18, 2019

(54) PROCESS FOR PURIFYING A STREAM COMPRISING 1,4-BUTANEDIOL

(75) Inventors: Graham Reed, London (GB); Paul Gordon, Durham (GB)

(73) Assignee: Johnson Matthey Davy Technologies Limited, London, England (GB)

( * ) Notice: Subject to any disclaimer, the term of this patent is extended or adjusted under 35 U.S.C. 154(b) by 317 days.

(21) Appl. No.: 14/343,284

(22) PCT Filed: Aug. 21, 2012

(86) PCT No.: PCT/GB2012/052048
§ 371 (c)(1),
(2), (4) Date: Jul. 2, 2014

(87) PCT Pub. No.: WO2013/034881
PCT Pub. Date: Mar. 14, 2013

(65) Prior Publication Data
US 2014/0350308 A1 Nov. 27, 2014

(30) Foreign Application Priority Data
Sep. 9, 2011 (GB) .................................. 1115617.1

(51) Int. Cl.
C07C 29/90 (2006.01)
C07C 29/84 (2006.01)
C07C 29/80 (2006.01)
B01D 3/00 (2006.01)
B01D 3/14 (2006.01)

(52) U.S. Cl.
CPC .............. *C07C 29/90* (2013.01); *B01D 3/002* (2013.01); *B01D 3/009* (2013.01); *B01D 3/14* (2013.01); *C07C 29/80* (2013.01); *C07C 29/84* (2013.01); *Y02P 20/127* (2015.11)

(58) Field of Classification Search
CPC .................................................... C07C 29/88
USPC ......................................................... 568/914
See application file for complete search history.

(56) References Cited

U.S. PATENT DOCUMENTS

| 4,584,419 A | 4/1986 | Sharif et al. |
| 4,751,334 A | 6/1988 | Turner et al. |
| 4,795,824 A | 1/1989 | Kippax et al. |
| 5,030,328 A * | 7/1991 | Fischer ................ C07D 315/00 203/78 |
| 5,310,954 A | 5/1994 | Hiles et al. |
| 6,137,016 A * | 10/2000 | Wood ...................... C07C 29/88 568/868 |
| 2010/0101931 A1 | 4/2010 | Pinkos et al. |

FOREIGN PATENT DOCUMENTS

| CA | 2226534 | 7/1998 | |
| EP | 0601571 A1 * | 6/1994 | ............ C07C 29/80 |
| EP | 0601571 A1 | 6/1994 | |
| EP | 1280787 B1 | 3/2001 | |
| JP | S61197534 A | 9/1986 | |
| JP | 2003026622 A | 1/2003 | |
| JP | 2003048854 A | 2/2003 | |
| KR | 20090110879 A | 10/2009 | |
| WO | 8800937 A1 | 2/1988 | |
| WO | 9008127 A1 | 7/1990 | |
| WO | 2006037957 A1 | 4/2006 | |

OTHER PUBLICATIONS

International Search Report Issued in PCT/GB2012/052048, dated Oct. 16, 2012, 3 pages.
International Preliminary Report on Patentability issued in PCT/GB2012/052048, dated Mar. 20, 2014, 9 pages.

* cited by examiner

*Primary Examiner* — Jeffrey S Lundgren
*Assistant Examiner* — Michael J Schmitt
(74) *Attorney, Agent, or Firm* — BakerHostetler

(57) ABSTRACT

A crude product stream of 1,4-butandiol and one or more of γ-butyrolactone, 2-(4-hydroxybutoxy)-tetrahydrofuran, 4-hydroxybutyl(4-hydroxybutyrate), and 3-(4-hydroxybutoxy)-tetrahydrofuran is supplied to a first distillation column. A side-draw of 1,4-butanediol and light components is removed, with the light components including at least some of those produced by reaction in the first distillation column. The stream is passed to a hydrogenation zone and subjected to hydrogenation in the presence of a hydrogenation catalyst. A 1,4-butanediol product stream having a reduced content of 2-(4-hydroxybutoxy)-tetrahydrofuran is recovered and passed to a second distillation column operated such that (4-hyroxybutyl)-4-hydroxybutyrate is removed as a bottom stream and a 1,4-butanediol stream is removed as overhead. The overhead stream removed is passed to a third distillation column and a purified 1,4-butanediol stream is recovered.

15 Claims, 5 Drawing Sheets

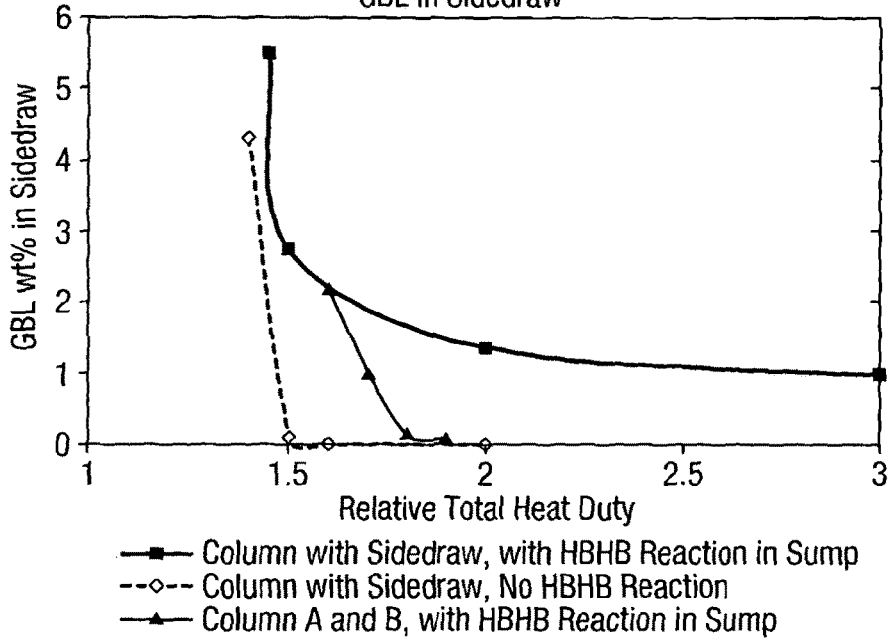
Fig. 5  Example 1 - Column A and B
GBL in Sidedraw
— ■ — Column with Sidedraw, with HBHB Reaction in Sump
-- ◇ -- Column with Sidedraw, No HBHB Reaction
— ▲ — Column A and B, with HBHB Reaction in Sump
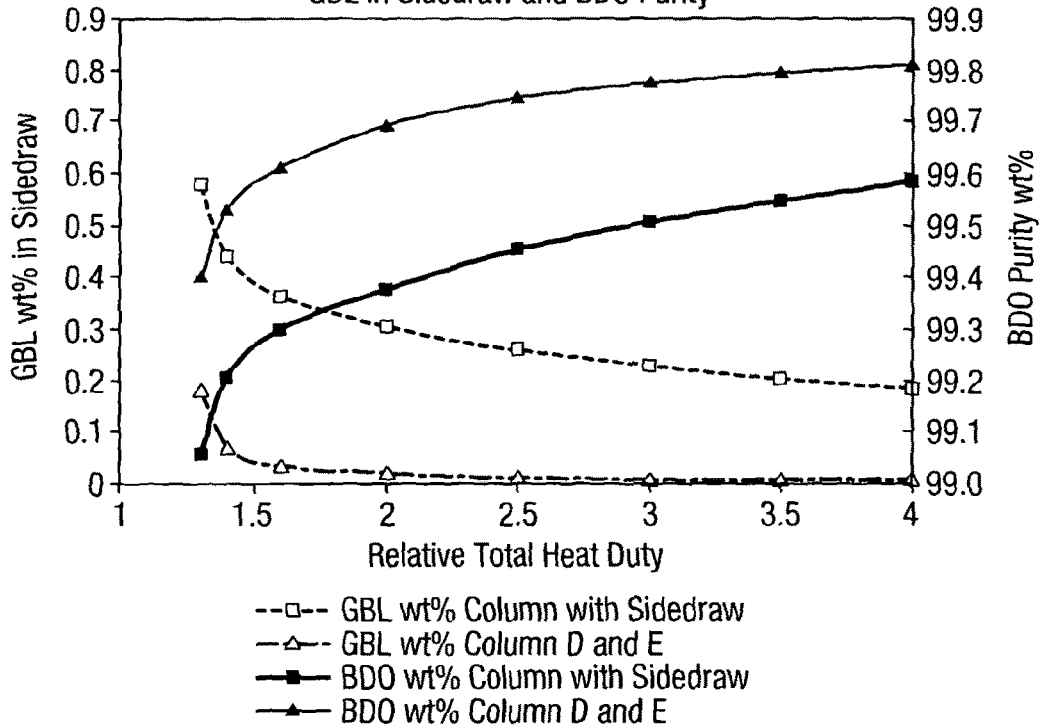
Fig. 6  Example 2 - Column D and E
GBL in Sidedraw and BDO Purity
-- □ -- GBL wt% Column with Sidedraw
-- △ -- GBL wt% Column D and E
— ■ — BDO wt% Column with Sidedraw
— ▲ — BDO wt% Column D and E

PROCESS FOR PURIFYING A STREAM COMPRISING 1,4-BUTANEDIOL

The present invention relates to a process for separating 1,4-butanediol. In particular, it relates to a process for separating 1,4-butanediol from a product stream from a reactor in which a hydrocarbon feedstock comprising maleic acid, maleic anhydride, mono- or di-($C_1$ to $C_4$) alkyl maleate or mixtures thereof is reacted with a hydrogen rich stream.

Whilst several synthetic routes to 1,4-butanediol are known, one process for the production of 1,4-butanediol uses maleic anhydride as a starting material. This is esterified with an alkanol, usually a $C_1$ to $C_4$ alkanol, such as methanol or ethanol, to yield the corresponding dialkyl maleate which is then subjected to hydrogenolysis to yield 1,4-butanediol and the alkanol. The alkanol may be recycled to the esterification reaction to produce further dialkyl maleate. Processes and plant for the production of dialkyl maleates from maleic anhydride are described in, for example, U.S. Pat. No. 4,795,824 and WO90/08127 which are incorporated herein by reference. The hydrogenolysis of dialkyl maleates to yield 1,4-butanediol is discussed in, for example, U.S. Pat. Nos. 4,584,419, 4,751,334 and WO88/00937 the disclosures of which are incorporated herein by reference.

The hydrogenolysis of the dialkyl maleate, such as dimethyl maleate or diethyl maleate, may also lead to the production of amounts of the valuable co-products, γ-butyrolactone and tetrahydrofuran. Since there is a ready market for these by-products, their co-production with 1,4-butanediol may not be disadvantageous. However, they must be separated from the 1,4-butanediol. These co-products may also be present in product streams from other processes used to produce 1,4-butanediol.

The product mixture will normally also contain other components. For example, it will normally contain minor amounts of the dialkyl succinate corresponding to the dialkyl maleate where the diester is used as the starting material, succinic acid, where maleic acid is used as the starting material etc. In addition, the alkanol used in the esterification will be present together with n-butanol, the corresponding dialkyl alkoxysuccinate, water and other impurities such as 2-(4-hydroxybutoxy)-tetrahydrofuran.

The various components and products are normally separated and purified by a number of distillation steps using conventional distillation arrangements. Where the process relates to the production of 1,4-butanediol with tetrahydrofuran and γ-butyrolactone from a feed comprising dialkylmaleate, the tetrahydrofuran is generally removed first as described in, for example, U.S. Pat. No. 5,310,954, which is incorporated herein by reference.

Lighter components such as alkanols and water are then removed by conventional distillation. The remaining mixture can then be further distilled to recover the 1,4-butanediol product and the γ-butyrolactone. Again this can be carried out by conventional distillation means which can include top, bottom and side draw arrangements.

Other arrangements, for example the use of a divided wall column, can be used. One example of the use of a divided wall column for this separation can be found in EP1280787 which is incorporated herein by reference.

As discussed above, 2-(4-hydroxybutoxy)-tetrahydrofuran is a by-product of the reaction to form 1,4-butanediol. This is a major contaminant of butanediol and is difficult to remove by distillation. It is therefore generally removed by reactive means such as those described in, for example, U.S. Pat. No. 6,137,016 and EP1794109.

The inventors have found that mixtures of some or all of 1,4-butanediol, tetrahydrofuran, γ-butyrolactone, alkanols and water are reactive at the conditions at which conventional distillations are carried out. Without wishing to be bound by any theory, it is believed that this reactivity increases the problems associated with separating the components of the mixture by the distillation means described in the prior art. It is therefore difficult to obtain the desired 1,4-butanediol in high purity. In this connection, "high purity" is generally considered to be purities in the region of about 99 wt % and above, preferably above 99.5 wt % and may be of the order of about 99.8 wt % and above.

Specifically, in prior art arrangements, reactions can occur in both the hydrogenation steps and in the distillation steps. These reactions can produce a range of heavy and light components. Examples of heavy components formed include transesters, such as hydroxybutylmethyl succinate, and heavy ethers, for example bis(4-hydroxy)dibutyl ether.

In addition, of particular importance is the formation of 4-hydroxybutyl (4-hydroxybutyrate) from butanediol and γ-butyrolactone. The formation of 4-hydroxybutyl (4-hydroxybutyrate) is an equilibrium reaction in which the 4-hydroxybutyl (4-hydroxybutyrate) can revert to 1,4-butanediol and γ-butyrolactone under certain conditions.

We have found that in the distillation arrangements of the prior art these heavy components fractionate in the bottom of conventional or divided wall columns. In the high temperature and high residence time regions of the column reboiler and sump, components such as 4-hydroxybutyl (4-hydroxybutyrate) react to reform to lighter components including γ-butyrolactone.

The problem with conventional distillation arrangements is that the light components, such as γ-butyrolactone, which are the result of the reaction in, for example, the sump, cannot be removed overhead from systems having conventional side draw arrangements. This is because the light components that are produced by the reaction of the heavy components in the column sump travel back up the column and contaminate the product side draw with light components and thereby limit the purity of the product that can be removed at the side draw. This would not normally be a problem in non-reactive mixtures where complete removal of light components would normally be expected in the stripping section of the column between the column feed and the product draw.

A similar problem is also encountered where a divided wall arrangement, such as that described in EP1280787, is used for the distillation. Here reaction of heavy components in the sump of the column produces light components which will travel to the product side of the divided wall and contaminate the product side draw with light components. Again this problem would not occur in non-reactive mixtures.

It will therefore be understood that in the distillation arrangements of the prior art it has not been possible to obtain the highest purity 1,4-butanediol due to the presence of these light components. The Applicants have identified that it is the reactive nature of the mixture which leads to the problems noted in the prior art.

In the hydrogenation of esters, such as those described in, for example, U.S. Pat. Nos. 4,584,419, 4,751,334 and WO88/00937, 3-(4-hydroxybutoxy)-tetrahydrofuran is formed as an impurity. It will be understood that this is a different from the 2-(4-hydroxybutoxy)-tetrahydrofuran discussed above and described in U.S. Pat. No. 6,137,016 and EP1794109. We have found that the 3-(4-hydroxybutoxy)-tetrahydrofuran does not react with the catalysts described in U.S. Pat. No. 6,137,016 and EP1794109 and it is resilient to removal by other reaction methods. The 3-(4-hydroxybutoxy)-tetrahydrofuran can only be removed by distillation. However, the 3-(4-hydroxybutoxy)-tetrahydrofuran is a close boiler to 1,4-butanediol making separation difficult. The inventors have found that the separation is particularly problematic in the presence of γ-butyrolactone.

In addition, the inventors have found that in the catalytic process described in U.S. Pat. No. 6,137,016 the 1,4-butanediol forms 4-hydroxybutyl(4-hydroxybutyrate) at an accelerated rate when in the presence of γ-butyrolactone thereby exacerbating the problem. In a similar mechanism to that described above, this 4-hydroxybutyl(4-hydroxybutyrate) will fractionate to the bottom of the distillation equipment and will react in the sump to form γ-butyrolactone. This γ-butyrolactone will contaminate the side draw in conventional distillation arrangements or divided wall processes as described above. In addition, the presence of this additional γ-butyrolactone will render it more difficult to remove the 3-(4-hydroxybutoxy)-tetrahydrofuran in the final 1,4-butanediol distillation column and hence further limit the purity of the 1,4-butanediol available by conventional separation processes.

The inventors have identified the reactive nature of the mixture and the reactions which occur in the sump, and the resultant contamination of product side draw and divided wall arrangements with γ-butyrolactone and the issues associated with the presence of 3-(4-hydroxybutoxy)-tetrahydrofuran in the reaction mixture and the effect of the presence of γ-butyrolactone on the separation.

The inventors have also found that when higher amounts of co-products γ-butyrolactone and tetrahydrouran are produced then the level of impurities in the 1,4-butanediol increases making it more difficult to produce high purity 1,4-butanediol. The presence of 4-hydroxybutyl(4-hydroxybutyrate) can also increase in these circumstances, increasing the effect of the rective nature of the mixture on the product purity achievable.

Having identified these problems, there is a need to provide a process which will enable these issues to be addressed and a high purity product to be achieved. In particular, it is desirable to provide a process which enables 1,4-butanediol having a purity of at least about 99 wt %, preferably about 99.5 wt % or above, most preferable in excess of 99.8 wt % and even of 99.9 wt % to be obtained. This has not been possible heretofore. The inventors have now identified that this is due to the reactive nature of the mixture from which the 1,4-butanediol is to be distilled which in turn is due to the presence of 3-(4-hydroxybutoxy)-tetrahydrofuran and to the effect of the presence of γ-butyrolactone whether present in the product mixture or generated in the reaction(s) occurring in the sump of the distillation column. It is therefore desirable to address one or more of these issues which effect the purity of the 1,4-butanediol obtainable. It is particularly desirable to address all of these issues.

The inventors have found that these problems can be addressed by the provision of a novel combination of distillation columns and reactions systems.

There is therefore provided a process for purifying a stream comprising 1,4-butanediol comprising the steps of:
(a) supplying a crude product stream comprising 1,4-butandiol and one or more of γ-butyrolactone, 2-(4-hydroxybutoxy)-tetrahydrofuran, 4-hydroxybutyl(4-hydroxybutyrate), and 3-(4-hydroxybutoxy)-tetrahydrofuran to a first distillation column;

(b) removing a side-draw comprising 1,4-butanediol, and light components, said light components including at least some of those produced by reaction in the first distillation column;
(c) passing the stream to a hydrogenation zone;
(d) subjecting the stream from step (c) to hydrogenation in the hydrogenation zone in the presence of a hydrogenation catalyst, and recovering from the hydrogenation zone a 1,4-butanediol product stream having a reduced content of 2-(4-hydroxybutoxy)-tetrahydrofuran, and optionally additionally including (4-hyroxybutyl)-4-hydroxybutyrate formed by reaction of γ-butyrolactone;
(e) passing the 1,4-butaendiol product stream from step (d) to a second distillation column operated such that (4-hyroxybutyl)-4-hydroxybutyrate is removed as a bottom stream and removing a 1,4-butanediol stream as overhead; and
(f) passing the overhead stream removed in (e) to a third distillation column and recovering a purified 1,4-butanediol stream.

By the process of the present invention a purified 1,4-butanediol stream is obtained. In a preferred process of the present invention, purities of at least about 99 wt %, preferably at least about 99.5 wt %, most preferably at least about 99.8 wt % and even of 99.9 wt % will be achieved. These levels of purity are not generally obtainable by conventional distillation arrangements or those involving divided wall column arrangements.

Removal of γ-butyrolactone from the first distillation column in the side draw results in the reduction of the formation of 4-hydroxybutyl(4-hydroxybutyrate) in the hydrogenation zone.

Further distillation to remove the 4-hydroxybutyl(4-hydroxybutyrate) before the final distillation column offers various advantages. These measures will in turn reduce the contamination of the final 1,4-butanediol distillation column with γ-butyrolactone either from γ-butyrolactone in the feed to the final distillation column or by reaction of 4-hydroxybutyl(4-hydroxybutyrate) in the sump of the final distillation column. These measures will also improve the removal of 3-(4-hydroxybutoxy)-tetrahydrofuran from the product 1,4-butanediol.

The crude product stream fed to the first distillation column may have any suitable composition and may include other impurities. The amount of different components in the stream may vary. In one arrangement the amount of 2-(4-hyroxybutoxy)-tetrahydrofuran content may be up to about 1 wt % or even higher.

The side draw from the first distillation column can be taken at any suitable point. In one arrangement, it will be taken from a point above the point at which the feed is added to the column.

In a preferred arrangement, the side draw from the first distillation column may be passed to a further distillation column before being passed to the hydrogenation zone. In this arrangement, the process additionally includes the step of: (b1) passing the side draw to the hydrogenation zone via a further distillation column in which at least some of the light components are stripped from the stream before it is passed to the hydrogenation zone.

It will be understood that where a further distillation column is present, further lights may be formed therein due to the reactions occurring in the sump thereof. At least a portion of these will generally be removed by the stripping process.

The first and further distillation columns, where present, may be combined into a single vessel. This may be achieved by any suitable means. In one arrangement, a separating baffle will divide the vessel into two columns for at least a portion of the length of the vessel. The baffle, where present, will extend to the bottom of the vessel and will generally be sealed thereto. In this arrangement, the side draw from the first distillation column, will be achieved via any suitable means including overflow over the baffle. In an alternative arrangement a draw may be taken from the first column, ie the first side of the column and fed back on the other side of the baffle.

Similarly, the second and third distillation columns may be combined into a single vessel. This may be achieved by any suitable means. In one arrangement, a separating baffle will divide the vessel into two columns for at least a portion of the length of the vessel. The baffle, where present, will extend to the bottom of the vessel and will generally be sealed thereto. In this arrangement, the side draw from the first distillation column, will be achieved via any suitable means including overflow over the baffle. In an alternative arrangement a draw may be taken from the first column, i.e. the first side of the column and fed back on the other side of the baffle. A purge will generally be taken from the bottom of the first distillation column to remove heavies.

A recycle from the second and/or third distillation column may be fed to the first distillation column. Where recycle streams are present they may be fed directly to the first distillation column or may be mixed with the crude feed stream prior to addition to the first distillation column. In one arrangement, at least some of the recycle stream may be fed directly to the first distillation column with the remainder being added to the feed stream.

The recycle from the third distillation column may be taken from any suitable point. In one arrangement, a recycle stream may be taken from the bottom of the third distillation column. A second recycle stream may be taken from the top of the third distillation column. These recycle streams may be combined before being returned to the first distillation column and they may be supplied separately and optionally to different parts of the distillation column.

At least some of the light components present in the side draw taken from the first distillation column will be separated in the further distillation column, where present, and may be returned to the first distillation column. They may be returned to any suitable point and will generally be returned to a point in the first distillation column where the side draw is taken.

The step of carrying out hydrogenation in step (c) may be carried out by any suitable means. In one arrangement, it may be carried out in accordance with the process described in U.S. Pat. No. 6,137,016 which is incorporated herein by reference. In one arrangement, the hydrogenation is carried out in the presence of from about 0.5 wt % up to about 15 wt %, based upon the weight of 1,4-butanediol to the hydrogenation zone, of water.

Any suitable hydrogenation catalyst may be used. The hydrogenation catalyst is preferably a Group VIII metal-containing hydrogenation catalyst. Suitable Group VIII metal-containing catalysts typically contain from about 0.1 wt % up to about 2 wt % of a Group VIII metal or metals. Examples of Group VIII metals include nickel, palladium, platinum, rhodium, iridium, rhenium and the like, as well as mixtures of two or more thereof. The Group VIII metal or metals is, or are, deposited on an inert support, such as graphite, alumina, silica-alumina, silica, zirconia, thoria, a diatomaceous earth and the like. A particularly preferred catalyst is a nickel catalyst. This can contain, for example, from about 10 wt % up to about 60 wt % or more of nickel. Another is a palladium-on-carbon catalyst, preferably containing from about 0.1 wt % up to about 4 wt % of palladium.

Although the hydrogenation reaction can be conducted in the vapour phase, it is conveniently carried out as a liquid phase reaction, using either a slurry of the catalyst or, more preferably, a fixed bed of catalyst. When operating with a fixed bed of catalyst the catalyst particles preferably have a particle size in the range of from about 0.5 mm to about 5 mm. The particles may be of any convenient shape, such as spheres, pellets, rings or saddles.

When using a fixed bed of catalyst the reactor may be a shell-and-tube reactor, which can be operated isothermally. However, it is preferably an adiabatic reactor. The use of an adiabatic reactor is advantageous since its capital cost is much lower than that of a shell-and-tube reactor and it is generally much easier to charge with the chosen catalyst.

The hydrogenation reaction may be carried out at any suitable reaction conditions. In one arrangement, hydrogenation may be conducted at an elevated temperature of, for example, from about 30° C. to about 170° C. The feed temperature to the hydrogenation zone may be from about 50° C. to about 125° C. The hydrogenation may be carried out at an elevated pressure. Suitable pressures include those of, for example, from about 50 psia (about 3.45 bar) to about 2000 psia (about 137.90 bar), preferably from about 150 psia (about 10.34 bar) up to about 1000 psia (about 68.95 bar).

The feed to the hydrogenation zone may be supplied at a liquid hourly space velocity of from about 0.1 $h^{-1}$ to about 4.0 $h^{-1}$, preferably from about 0.5 $h^{-1}$ to about 1.5 $h^{-1}$.

The feed to the hydrogenation zone may be mixed with an inert diluent prior to feed to the hydrogenation zone. In one arrangement, the inert diluent may be a recycle from the exit from the hydrogenation zone. In this arrangement, the ratio of inert diluent to fresh feed preferably lies in the range of from about 1:1 to about 1000:1.

The distillation columns may be operated under the same or different conditions. In one arrangement, they may be operated at pressures of from about 0.1 to about 1 bar abs, preferably from about 0.1 to about 0.3 bar abs. Suitable temperatures include those of from about 100° C. to about 250° C., preferably from about 120° C. to about 220° C.

The distillation columns may include trays or structured packing. In one arrangement the columns contain from about 10 to about 100 theoretical stages, preferably from about 15 to about 80 theoretical stages.

The present invention will now be described by way of example with reference to the accompanying drawings in which:

FIG. 5 is a graph referred to in Example 1; and

FIG. 6 is a graph referred to in Example 2.

It will be understood that the drawings are diagrammatic and that further items of equipment such as reflux drums, pumps, compressors, vacuum pumps, temperature sensors, pressure sensors, pressure relief valves, control valves, flow controllers, level controllers, holding tanks, storage tanks and the like may be required in a commercial plant. The provision of such ancillary items of equipment forms no part of the present invention and is in accordance with conventional chemical engineering practice.

Figure 1:
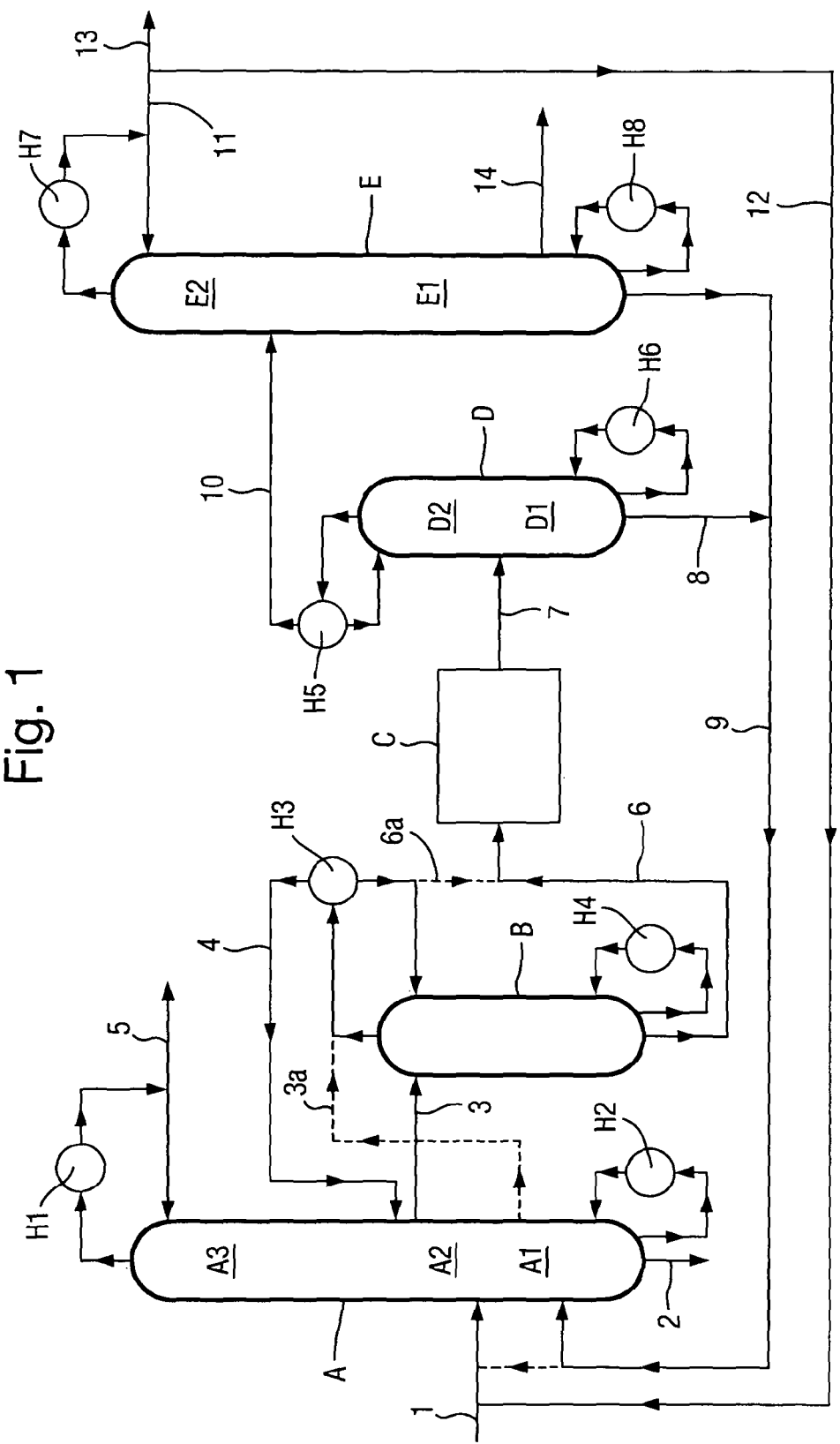
FIG. 1 is a simplified schematic representation of one arrangement for the process of the present invention.

As illustrated in FIG. 1, a feed stream is fed in line 1. In one arrangement this feed stream will comprise butanediol, γ-butyrolactone, dialkyl alkoxysuccinate, transesters such as 4 hydroxybutyl methyl succinate, heavy ethers such as bis(4-hydroxy)dibutyl ether, 4-hydroxybutyl (4-hydroxybutyrate), 2-(4 hydroxybutoxy)-tetrahydrofuran, 3-(4 hydroxybutoxy)-tetrahydrofuran, other minor impurities and residual alkanols, tetrahydrofuran and water. This stream is fed to distillation column A. A recycle stream 9 containing heavy components from downstream units can also be fed to first distillation column A. This recycle stream may be fed to first distillation column A at the same point as feed stream 1 and/or it may be supplied to the column at a different point, which will generally be lower than the point at which stream 1 is fed to first distillation column A.

The heavy components in the feed 1 and recycle stream 9 will concentrate in section A1 of the first distillation column and are removed in purge stream 2. The heavy components concentrating in section A1 will include 4-hydroxybutyl (4-hydroxybutyrate) which will react in the sump to reform to 1,4-butanediol, and γ-butyrolactone. The γ-butyrolactone, being lighter, will then travel back up the column.

The concentration of heavy components, including 4-hydroxybutyl (4-hydroxybutyrate) will reduce in section A2 of the column thereby reducing the heavy component content in the product side draw 3. The stream removed in side draw will include the γ-butyrolactone formed in the sump by the reaction of 4-hydroxybutyl (4-hydroxybutyrate).

In one arrangement, the side draw 3 is taken from above the feed stream 1. At least some of the light components from the feed stream will also be present in the stream removed by the side draw 3. This stream is passed to the further distillation column B where they are at least partially removed and returned to distillation column A via stream 4.

Reflux for the further distillation column B is provided by a partial condenser H3. By this combination of distillation columns, the light and heavy components in the feed and the light components produced by reaction in the sump of the first distillation column A are removed and therefore the stream 6 removed from the bottom of the further distillation column B has a reduced content of these components.

In an alternative arrangement the side draw can be taken at a point below the point of entry of feed stream 1. This lower side draw is illustrated in FIG. 1 as line 3a. This stream is then partially condensed in the condenser H3, without being passed through further distillation column B. This will reduce the light component content of the stream 6a, but only partially reduce the heavy component content of the stream 6a. Whether or not the further distillation column B is present the remaining light components, including γ-butyrolactone, dialkyl alkoxysuccinate, and residual alkanols, tetrahydrofuran and water are concentrated in section A3 of distillation column A and removed in the overhead stream 5.

The stream 6 or 6a will contain the majority of the 2-(4 hydroxybutoxy)-tetrahydrofuran and 3-(4 hydroxybutoxy)-tetrahydrofuran from the feed stream 1. The 2-(4 hydroxybutoxy)-tetrahydrofuran is removed in the hydrogenation zone C as described in U.S. Pat. No. 6,137,016. Residual γ-butyrolactone in stream 6 or 6a will react to 4-hydroxybutyl (4-hydroxybutyrate) in the hydrogenation zone C. However the γ-butyrolactone content of stream 6 and hence the amount of 4-hydroxybutyl (4-hydroxybutyrate) made in hydrogenation zone (C) will be considerably less where the further distillation column B is present to reduce the lights content of stream 6 without taking into account the reaction of heavy components to light components in the sump of distillation column A.

The product 7 from the hydrogenation zone C is fed to the second distillation column D. The residual 4-hydroxybutyl (4-hydroxybutyrate) formed in the hydrogenation zone C is concentrated in section D1 of distillation column D, and purged from the bottom of the column via stream 8. Other impurities which may be present will also be concentrated in section D1. Stream 8 can be recycled to the first distillation column A via stream 9 to further recover 1,4-butanediol and further react the 4-hydroxybutyl (4-hydroxybutyrate) to reduce the loss of heavy material. Reflux for the second distillation column D is provided by partial condenser H5. The heavy components, including 4-hydroxybutyl (4-hydroxybutyrate) are removed in section D2 of column D. This significantly reduces the quantity of 4-hydroxybutyl (4-hydroxybutyrate) being fed to the third distillation column E in stream 10. The advantage of this is there will be less 4-hydroxybutyl (4-hydroxybutyrate) in the sump of the third distillation column E to react to γ-butyrolactone, and hence this will reduce the γ-butyrolactone content in the third distillation column E. This will assist in the separation of 3-(4 hydroxybutoxy)-tetrahydrofuran in the third distillation column E, which would otherwise be difficult to separate in the presence of significant quantities of γ-butyrolactone.

The 3-(4 hydroxybutoxy)-tetrahydrofuran, any residual γ-butyrolactone and other residual light components are removed in section E1 of the third distillation column E. The light components are concentrated in section E2 of the third distillation column E and removed overhead in stream 11. The overhead stream 11 can be recycled via stream 12 to the first distillation column A or via separation columns upstream of first distillation column A to recover 1,4-butanediol and γ-butyrolactone in stream 12. A purge stream 13 can be used to remove the light impurities including 3-(4 hydroxybutoxy)-tetrahydrofuran from this recycle. The product 1,4-butanediol is removed as a bottom stream 14 or preferably as a sidestream close to, or at, the bottom of third distillation column E.

Figure 2:
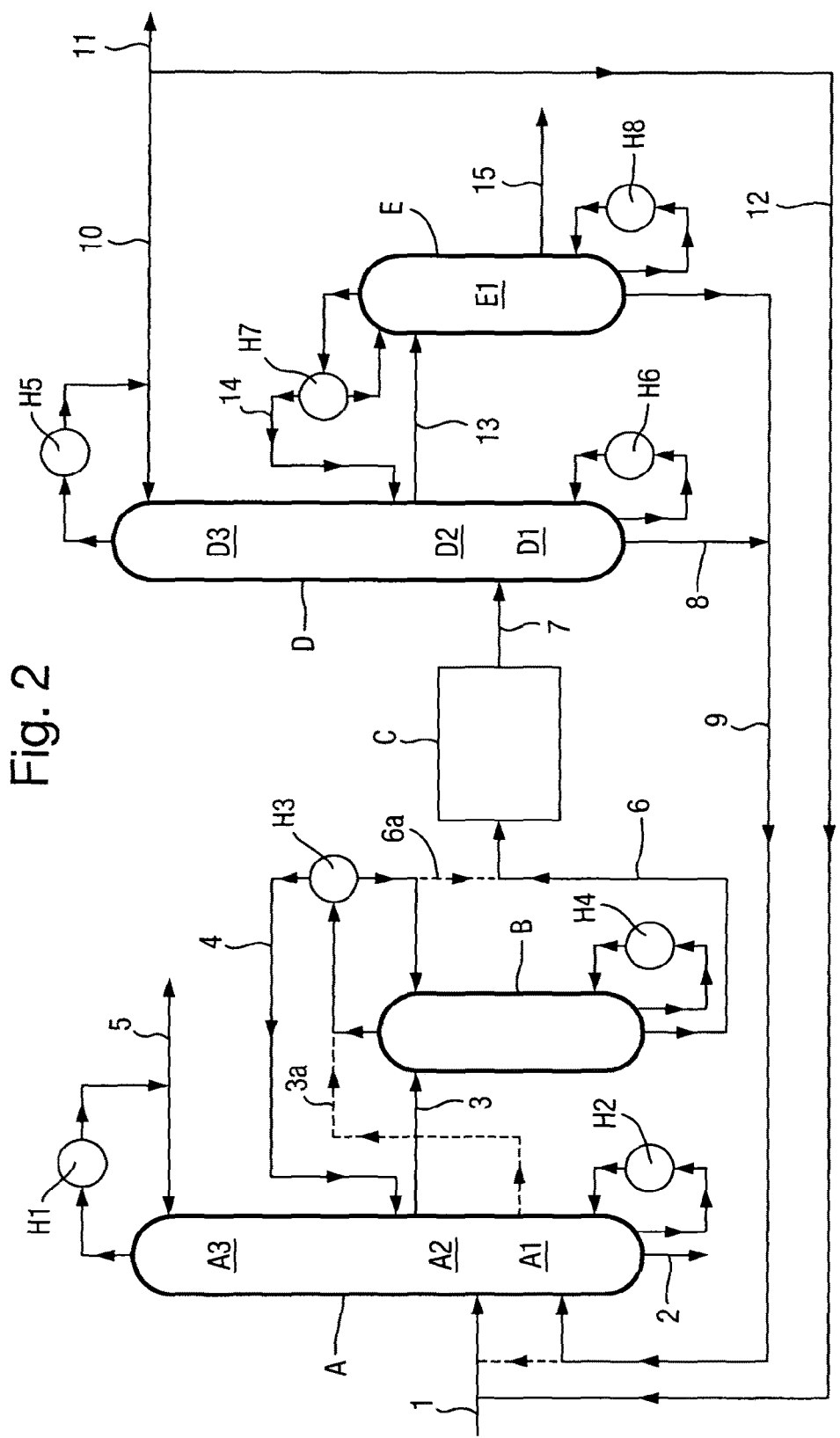
FIG. 2 is a simplified schematic representation of a second arrangement for the process of the present invention.

An alternative arrangement of the second and third distillation columns D and E is illustrated in FIG. 2. The scheme is the same as that of FIG. 1 up to the hydrogenation zone C. The product stream 7 from the hydrogenation zone C is fed to the second distillation column D. The residual 4-hydroxybutyl (4-hydroxybutyrate) formed in the hydrogenation zone C is concentrated in section D1 of the second distillation column D, and purged from the bottom of the column via stream 8. Other impurities which may be present will also be concentrated in section D1. Reflux for column D is provided by a condenser H5. The heavy components, including 4-hydroxybutyl (4-hydroxybutyrate) are removed in section D2 of the second distillation column D. A side draw 13 is taken from the second distillation column D above the feed stream 7 and fed to the third distillation column E. The 3-(4 hydroxybutoxy)-tetrahydrofuran, any residual γ-butyrolactone and other residual light components are removed in section E1 of the third distillation column E. Reflux for the third distillation column E is provided by a partial condenser H7 and the light components removed are fed to the second distillation column D via stream 14. The light components are concentrated in section D3 of the second distillation column D and removed overhead in stream 10. The product 1,4-butanediol 15 is removed as a bottom stream or preferably as a sidestream close to, or at, the bottom of the third distillation column E.

Figure 3:
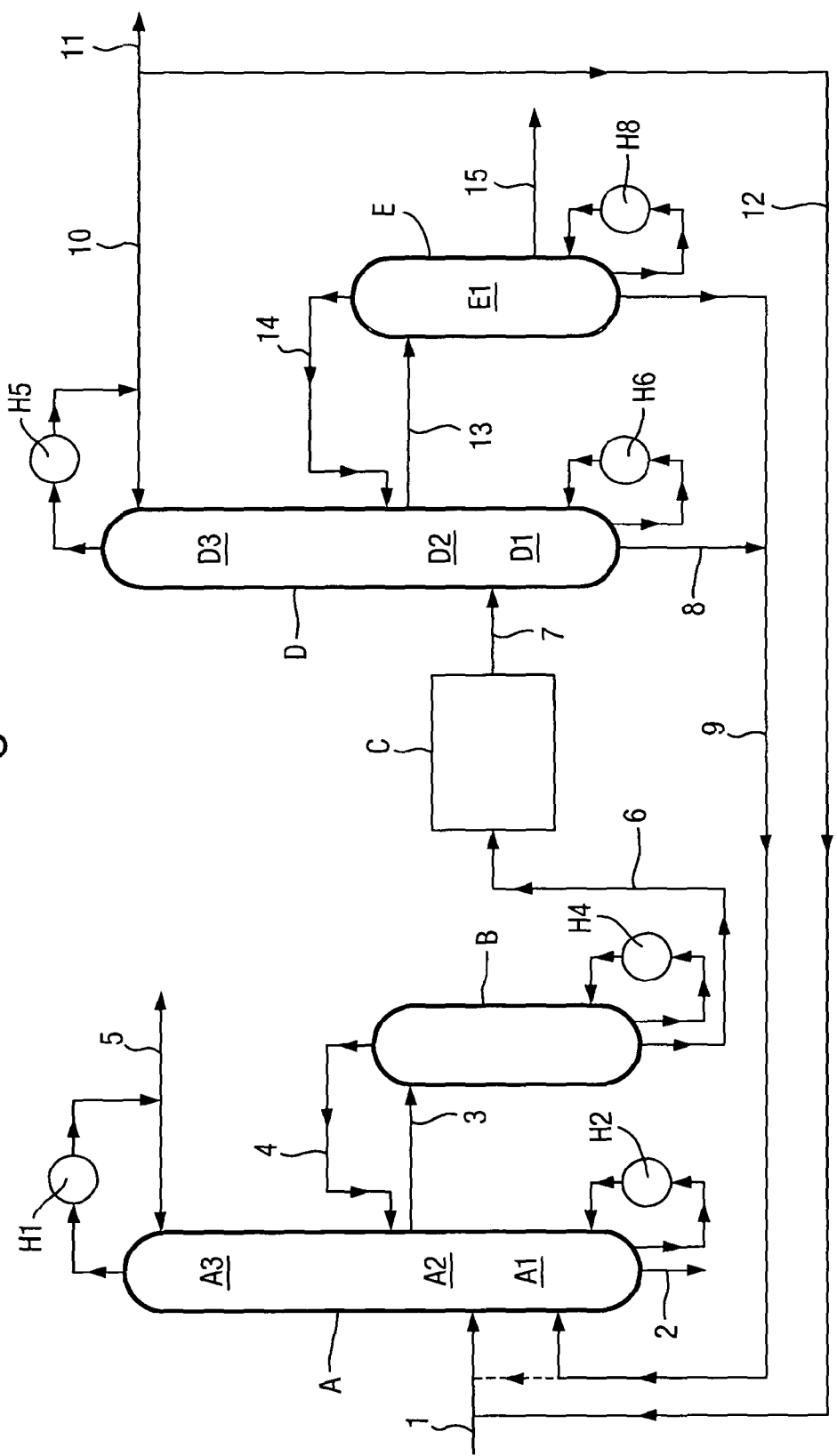
FIG. 3 is a simplified schematic representation of a third arrangement for the process of the present invention.

Alternative arrangements of distillation columns A, B, D and E can be used. One alternative arrangement is illustrated in FIG. 3. In this arrangement the duties of condensers H1 and H3 can be combined, and condensers H5 and H7 can be combined, saving on the number of installed equipment items. This is applicable to both schemes illustrated in FIGS. 1 and 2.

Figure 4:
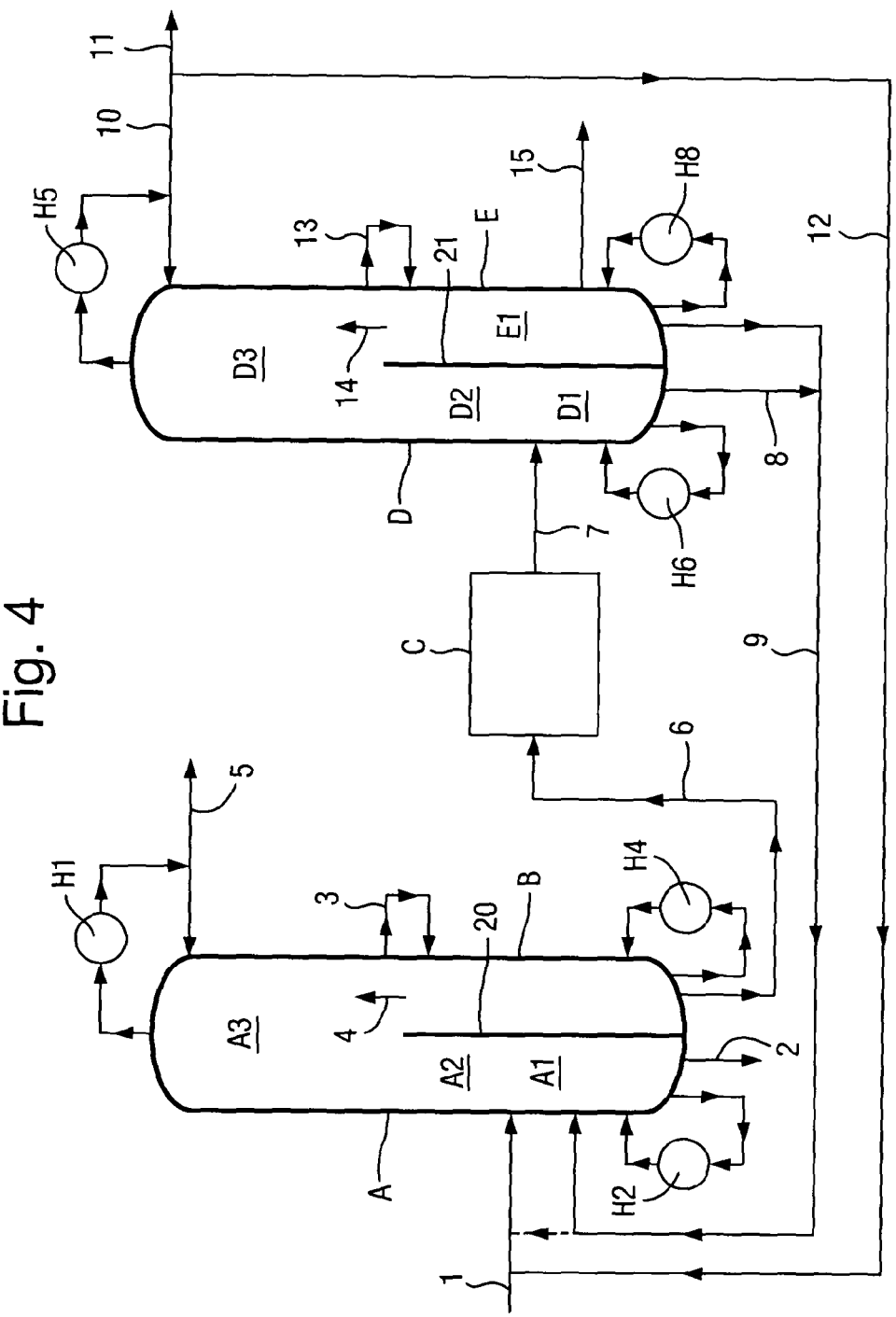
FIG. 4 is a simplified schematic representation of a fourth arrangement for the process of the present invention.

A further alternative arrangement of distillation columns A, B, D and E can be used and is illustrated in FIG. 4. In this arrangement the operations of first and further distillation columns A and B are combined into a single vessel by use of a sealed, separating baffle 20 which extends completely to the bottom of the vessel. The single vessel will require two reboilers, H2 and H4. Similarly second distillation column D and third distillation column E can be combined into a single vessel by use of a sealed, separating baffle 21 which extends completely to the bottom of the vessel. The single vessel has two reboilers H6 and H8. In terms of separation the schemes in FIGS. 3 and 4 are equivalent and hence the description and line numbers for FIG. 3 is the same for FIG. 4. Both schemes will achieve the removal of the light and heavy impurities in the feed stream 1 in conjunction with the light components produced as a product of reaction in the sumps of distillation columns A and C, to produce high purity 1,4-butanediol.

The present invention will now be discussed with reference to the following examples.

EXAMPLE 1

A fluid stream produced by the hydrogenation of dimethyl maleate containing approximately 15 wt % γ-butyrolactone and 4 wt % 4-hydroxybutyl(4-hydroxybutyrate) is fed to a distillation column with a side draw below the feed point. The graph set out in FIG. 5 illustrates the γ-butyrolactone content obtainable in the side draw, when the 4-hydroxybutyl(4-hydroxybutyrate) reacts in the sump of the column to produce 1,4-butanediol and γ-butyrolactone. There is a lower limit below which it is difficult to reduce this composition. This limit is dependent on the composition of 1,4-butanediol and γ-butyrolactone produced in the hydrogenation.

By way of comparison, the graph of FIG. 5 also illustrates the 4-hydroxybutyl(4-hydroxybutyrate) in the side draw if the 4-hydroxybutyl(4-hydroxybutyrate) did not react in the sump of the column. In this case, where distillative effects alone would determine composition, the γ-butyrolactone content is almost zero.

Also by way of comparison, the graph of FIG. 5 illustrates the γ-butyrolactone composition achievable in the product of the side draw from column A is taken above the feed and fed to a second column B. In this case the γ-butyrolactone is substantially reduced.

EXAMPLE 2

A fluid stream from the hydrogenation zone C containing approximately 1-1.5 wt % γ-butyrolactone and 1-1.5 wt % 4-hydroxybutyl(4-hydroxybutyrate) is fed to a distillation column with a side draw below the feed point. The stream also contains other light and heavy impurities and a reduced content of 2-(4-hydroxybutoxy)-tetrahydrofuran as a result of the reaction in hydrogenation zone C. The graph of FIG. 6 illustrates the γ-butyrolactone content obtainable in the side draw, when the 4-hydroxybutyl(4-hydroxybutyrate) reacts in the sump of the column to produce 1,4-butanediol and γ-butyrolactone, and the achievable product purity.

By way of comparison the graph also illustrates the γ-butyrolactone composition and product purity achievable if the side draw from column D is taken from above the feed and fed to a second column E. This illustrates that substantially higher purity can be achieved with this arrangement.

EXAMPLE 3

A stream of fluid containing 0.14 wt % 3-(4-hydroxybutoxy)-tetrahydrofuran, 0.25 wt % γ-butyrolactone and the remainder 1,4 butanediol and other impurities, was heated to the boiling point of the mixture. The mixture was then allowed to partially flash in a glass vessel at a vacuum pressure of 175 mbar. The vapour from this flash was condensed in a glass condenser and the resultant liquid collected and analysed. The liquid from the flash was also collected and analysed. Analysis was by gas chromatography. The vapour from this flash contained 0.18 wt % of 3-(4-hydroxybutoxy)-tetrahydrofuran, and 97.12 wt % of 1,4 butanediol. The liquid contained 0.13 wt % 3-(4-hydroxybutoxy)-tetrahydrofuran and 92.52 wt % of 1,4 butanediol. The volatility of 3-(4-hydroxybutoxy)-tetrahydrofuran relative to 1,4 butanediol in this mixture was 1.32.

A second similar stream of fluid containing 0.11 wt % 3-(4-hydroxybutoxy)-tetrahydrofuran, 15 wt % γ-butyrolactone and the remainder 1,4 butanediol and other impurities, was flashed in a similar manner. The vapour from this flash contained 0.076 wt % of 3-(4-hydroxybutoxy)-tetrahydrofuran and 52.6 wt % of 1,4 butanediol. The liquid contained 0.096 wt % 3-(4-hydroxybutoxy)-tetrahydrofuran and 77.98 wt % of 1,4 butanediol. The volatility of 3-(4-hydroxybutoxy)-tetrahydrofuran relative to 1,4 butanediol in this mixture was 1.17.

The higher volatility of 3-(4-hydroxybutoxy)-tetrahydrofuran relative to 1,4 butanediol at the lower γ-butyrolactone concentration illustrates that the separation of 3-(4-hydroxybutoxy)-tetrahydrofuran from 1,4 butanediol is easier at lower γ-butyrolactone concentration in the feed.

The invention claimed is:
1. A process for purifying a stream comprising 1,4-butanediol comprising the steps of:
 (a) supplying a crude product stream comprising (i) 1,4-butandiol, (ii) γ-butyrolactone, and (iii) one or more of 2-(4-hydroxybutoxy)-tetrahydrofuran,4-hydroxybutyl(4-hydroxybutyrate), and 3-(4-hydroxybutoxy)-tetrahydrofuran to a first distillation column;
 (b) removing a side-draw comprising 1,4-butanediol, and light components, said light components including at least some of those produced by reaction in the first distillation column;
 (c) passing the side-draw to a hydrogenation zone;
 (d) subjecting the stream from step (c) to hydrogenation in the hydrogenation zone in the presence of a hydrogenation catalyst, and recovering from the hydrogenation zone a 1,4-butanediol product stream having a reduced content of 2-(4-hydroxybutoxy)tetrahydrofuran;
 (e) passing the 1,4-butaendiol product stream from step (d) to a second distillation column operated such that (4-hydroxybutyl)-4-hydroxybutyrate is removed as a bottom stream and removing a 1,4-butanediol stream as overhead; and
 f) passing the overhead stream removed in (e) to a third distillation column to remove γ-butyrolactone formed in the sump of the column in step (e) and recovering therefrom a purified 1,4-butanediol.

2. The process according to claim 1 wherein the side draw from the first distillation column is taken from a point above the point at which the feed is added to the column.

3. The process according to claim 1 wherein the process additionally includes the step of:
(b1) passing the side draw to the hydrogenation zone via a further distillation column in which at least some of the light components are stripped from the stream before it is passed to the hydrogenation zone.

4. The process according to claim 3, wherein the first and further distillation columns are combined into a single vessel.

5. The process according to claim 4, wherein the vessel includes a separating baffle.

6. The process according to claim 1, wherein the second and third distillation columns are combined into a single vessel.

7. The process according to claim 6, wherein the vessel includes a separating baffle.

8. The process according to claim 1, wherein a recycle from the second and/or third distillation column is fed to the first distillation column.

9. The process according to claim 1, wherein the hydrogenation is carried out at a temperature of from about 30° C. to about 170° C.

10. The process according to claim 1, wherein the hydrogenation is carried out at a pressure of from about 3.45 bar (about 50 psia) to about 137.90 bar (about 2000 psia).

11. The process according to claim 1, wherein the feed to the hydrogenation zone is supplied at a liquid hourly space velocity of from about 0.1 $h^{-1}$ to about 4.0 $h^{-1}$.

12. The process according to claim 1, wherein the distillation columns are operated at pressures of from about 0.1 to about 1 bar abs.

13. The process according to claim 1, wherein the distillation columns are operated at temperatures of from about 100° C. to about 250° C.

14. The process according to claim 1, wherein the distillation columns contain from about 10 to about 100 theoretical stages.

15. The process according to claim 1, wherein the 1,4-butanediol product stream having a reduced content of 2-(4-hydroxybutoxy)-tetrahydrofuran further includes (4-hydroxybutyl)-4-hydroxybutyrate formed by reaction of γ-butyrolactone.

* * * * *